US011077257B2

United States Patent
Kemp

(10) Patent No.: US 11,077,257 B2
(45) Date of Patent: Aug. 3, 2021

(54) AUTOINJECTOR

(71) Applicant: Sanofi-Aventis Deutschland GMBH, Frankfurt am Main (DE)

(72) Inventor: Thomas Kemp, Ashwell (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 14 days.

(21) Appl. No.: 16/355,691

(22) Filed: Mar. 15, 2019

(65) Prior Publication Data
US 2019/0209788 A1 Jul. 11, 2019

Related U.S. Application Data

(63) Continuation of application No. 14/903,383, filed as application No. PCT/EP2014/064422 on Jul. 7, 2014, now Pat. No. 10,232,125.

(30) Foreign Application Priority Data

Jul. 9, 2013 (EP) ..................................... 13175659

(51) Int. Cl.
*A61M 5/32* (2006.01)
*A61M 5/20* (2006.01)
*A61M 5/50* (2006.01)

(52) U.S. Cl.
CPC ........ *A61M 5/3204* (2013.01); *A61M 5/2033* (2013.01); *A61M 5/326* (2013.01);
(Continued)

(58) Field of Classification Search
CPC .... A61M 2005/2013; A61M 2005/206; A61M 2005/3247; A61M 5/2033; A61M 5/326
See application file for complete search history.

(56) References Cited

U.S. PATENT DOCUMENTS

2010/0268170 A1 10/2010 Carrel et al.
2014/0207106 A1\* 7/2014 Bechmann .......... A61M 5/2033
604/506

FOREIGN PATENT DOCUMENTS

EP 2438942 4/2012
EP 2468335 6/2012
(Continued)

OTHER PUBLICATIONS

Extended European Search Report and Written Opinion in Application No. 13175659.5, dated Jan. 2, 2014, 8 pages.
(Continued)

*Primary Examiner* — Deanna K Hall
(74) *Attorney, Agent, or Firm* — Fish & Richardson P.C.

(57) ABSTRACT

An autoinjector includes a case, a needle shroud telescopically coupled to the case, a carrier slidably arranged in the case, a collar rotatably and slidably disposed in the case and coupled to the needle shroud and the carrier, and a trigger button operably coupled to the carrier. The case includes a rib. The needle shroud is movable between a first extended position, a retracted position, and a locked second extended position. The carrier is adapted to hold a medicament container and movable from a first axial position to a second axial position relative to the case. The carrier abuts the rib in the first axial position and the needle shroud is in the first extended position and disengages the rib when the needle shroud is in the retracted position and the trigger button is pressed to advance the carrier to the second axial position.

20 Claims, 14 Drawing Sheets

(52) U.S. Cl.
CPC ..... *A61M 5/5086* (2013.01); *A61M 2005/206* (2013.01); *A61M 2005/208* (2013.01); *A61M 2005/3247* (2013.01); *A61M 2205/581* (2013.01); *A61M 2205/582* (2013.01)

(56) References Cited

FOREIGN PATENT DOCUMENTS

| EP | 2489380 | 8/2012 |
|----|---------|--------|
| JP | 2010-540059 | 12/2010 |
| WO | WO 2009/063030 | 5/2009 |
| WO | WO 2013/034984 | 3/2013 |

OTHER PUBLICATIONS

International Preliminary Report on Patentability in International Application No. PCT/EP2014/064422, dated Jan. 12, 2016, 8 pages.
International Search Report and Written Opinion in International Application No. PCT/EP2014/064422, dated Nov. 5, 2014, 12 pages.

\* cited by examiner

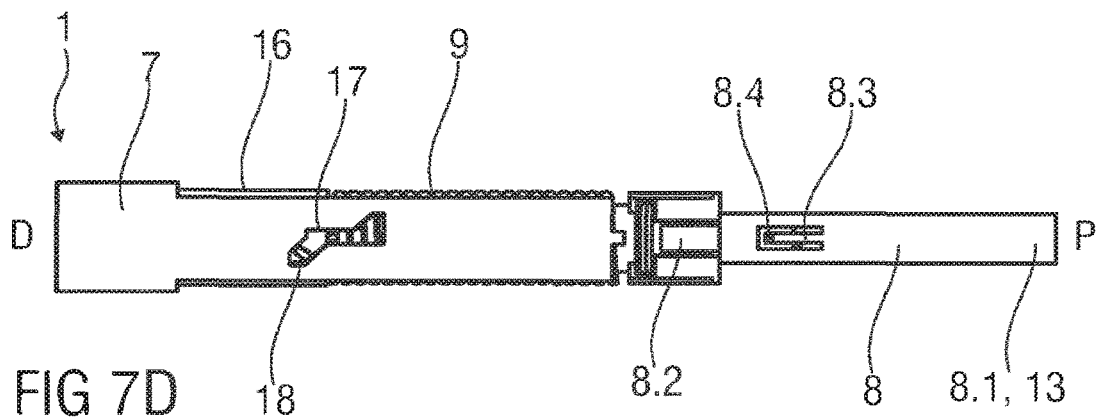
FIG 7D
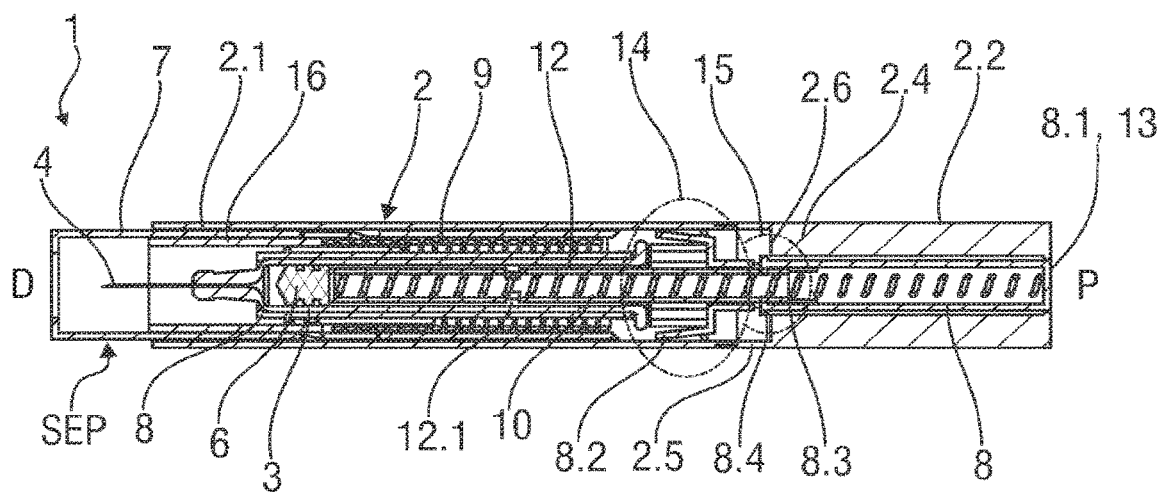
FIG 7E
FIG 7F

AUTOINJECTOR

CROSS-REFERENCE TO RELATED APPLICATIONS

This application is a continuation of U.S. patent application Ser. No. 14/903,383, filed Jan. 7, 2016, which is a U.S. national stage application under 35 USC § 371 of International Application No. PCT/EP2014/064422, filed on Jul. 7, 2014, which claims priority to European Patent Application No. 13175659.5, filed on Jul. 9, 2013, the entire contents of which are incorporated herein by reference.

TECHNICAL FIELD

The present disclosure relates to an autoinjector.

BACKGROUND

Administering an injection is a process which presents a number of risks and challenges for users and healthcare professionals, both mental and physical. Injection devices typically fall into two categories—manual devices and autoinjectors. In a conventional manual device, manual force is required to drive a medicament through a needle. This is typically done by some form of button/plunger that has to be continuously pressed during the injection. There are numerous disadvantages associated with this approach. For example, if the button/plunger is released prematurely, the injection will stop and may not deliver an intended dose. Further, the force required to push the button/plunger may be too high (e.g., if the user is elderly or a child). And, aligning the injection device, administering the injection and keeping the injection device still during the injection may require dexterity which some patients (e.g., elderly patients, children, arthritic patients, etc.) may not have.

Autoinjector devices aim to make self-injection easier for patients. A conventional autoinjector may provide the force for administering the injection by a spring, and trigger button or other mechanism may be used to activate the injection. Autoinjectors may be single-use or reusable devices.

There remains a need for an improved autoinjector.

SUMMARY

Certain aspects of the invention provide improved autoinjectors.

In an exemplary embodiment, an autoinjector according to some aspects of the present invention comprises a case including a rib, a needle shroud telescopically coupled to the case and movable between a first extended position, a retracted position and a locked second extended position, a carrier slidably arranged in the case, adapted to hold a medicament container, and movable from a first axial position to a second axial position relative to the case, a collar rotatably and slidably disposed in the case and coupled to the needle shroud and the carrier, and a trigger button operably coupled to the carrier. The carrier abuts the rib in the first axial position and the needle shroud is in the first extended position and disengages the rib when the needle shroud is in the retracted position and the trigger button is pressed to advance the carrier to the second axial position.

In an exemplary embodiment, the autoinjector further comprises a plunger slidably coupled to the carrier, and a drive spring biasing the plunger relative to the carrier. The carrier includes a compliant beam having a boss adapted to engage an opening in the plunger when the carrier is in the first axial position. The boss is adapted to engage the case when the carrier is in the second axial position.

In an exemplary embodiment, the collar includes a shroud boss adapted to engage a shroud slot in the needle shroud and a carrier boss adapted to engage a carrier slot in the carrier.

In an exemplary embodiment, the collar is in a first angular position relative to the case when the needle shroud is in the first extended position and the carrier is in the first axial position. The collar rotates to a second angular position relative to the case and translates proximally relative to the case when the needle shroud moves from the first extended position to the retracted position. The collar translates distally relative to the case when the needle shroud is in the retracted position and the carrier moves from the first axial position to the second axial position. The boss disengages the opening and abuts the case when the carrier is in the second axial position, and the plunger translates axially relative to the carrier under the force of the drive spring advancing the carrier from the second axial position to a third axial position relative to the case. The collar rotates to a third angular position relative to the case and translates with the needle shroud distally relative to the case when the carrier is in the third axial position. The collar rotates to a fourth angular position relative to the case when the needle shroud is in the locked second extended position. The carrier boss is adapted to abut a surface in the carrier slot when the collar is in the fourth angular position and the needle shroud is in the locked second extended position. The engagement of the carrier boss and the carrier slot notch and the engagement of the carrier to the case substantially fixes the collar in an axial position relative to the case.

In an exemplary embodiment, the autoinjector further comprises a control spring biasing the collar relative to the case.

In an exemplary embodiment, the carrier includes a compliant beam adapted to engage the rib when the carrier is in the first and second axial positions. The needle shroud includes a ramp adapted to engage and deflect the compliant beam as the needle shroud translates from the first extended position to the retracted position.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present disclosure will become more fully understood from the detailed description given hereinbelow and the accompanying drawings which are given by way of illustration only, and thus, are not limitive of the aspects of the present invention, and wherein:

FIG. 7D is a longitudinal section of an exemplary embodiment of an autoinjector after use, FIG. 7E is a longitudinal section of an exemplary embodiment of an autoinjector after use, and FIG. 7F is another longitudinal section of an exemplary embodiment of an autoinjector after use.

Corresponding parts are marked with the same reference symbols in all figures.

DETAILED DESCRIPTION

Figure 1A:
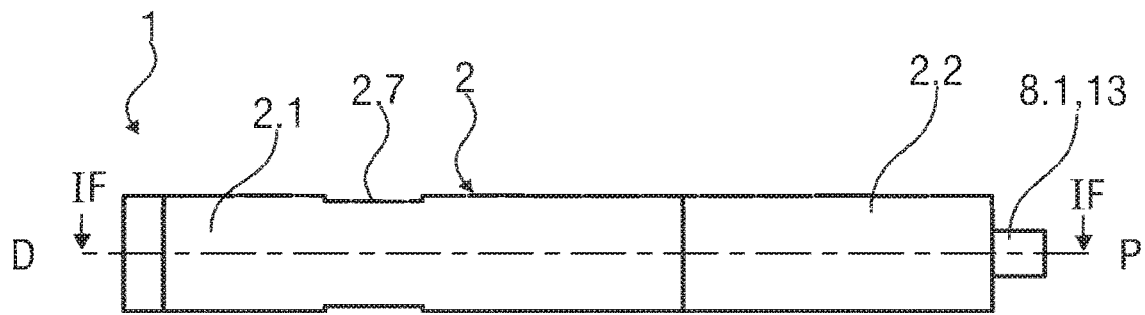
FIG. 1A is a side view of an exemplary embodiment of an autoinjector prior to use.
Figure 1B:
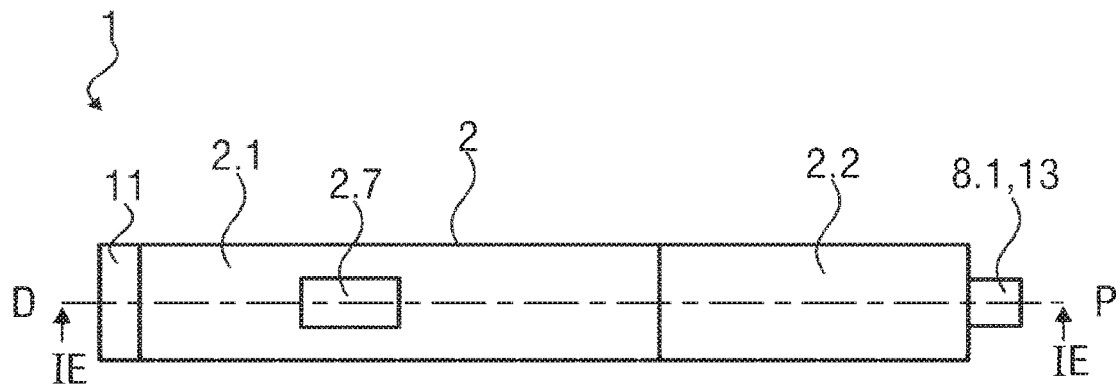
FIG. 1B is a side view of an exemplary embodiment of an autoinjector prior to use.
Figure 1C:
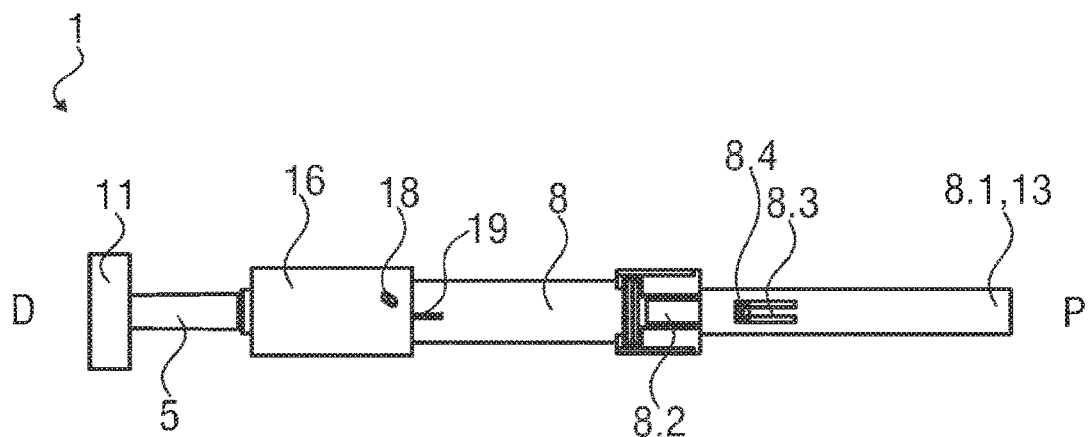
FIG. 1C is a longitudinal section of an exemplary embodiment of an autoinjector prior to use.
Figure 1D:
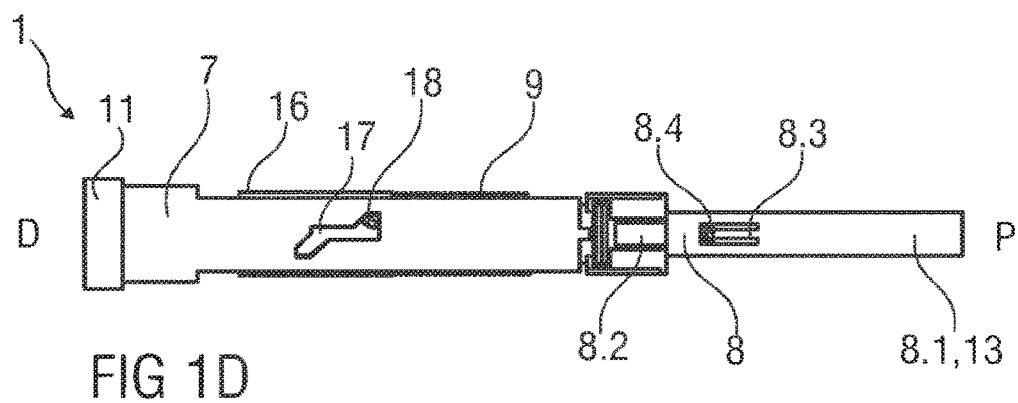
FIG. 1D is a longitudinal section of an exemplary embodiment of an autoinjector prior to use.
Figure 1E:
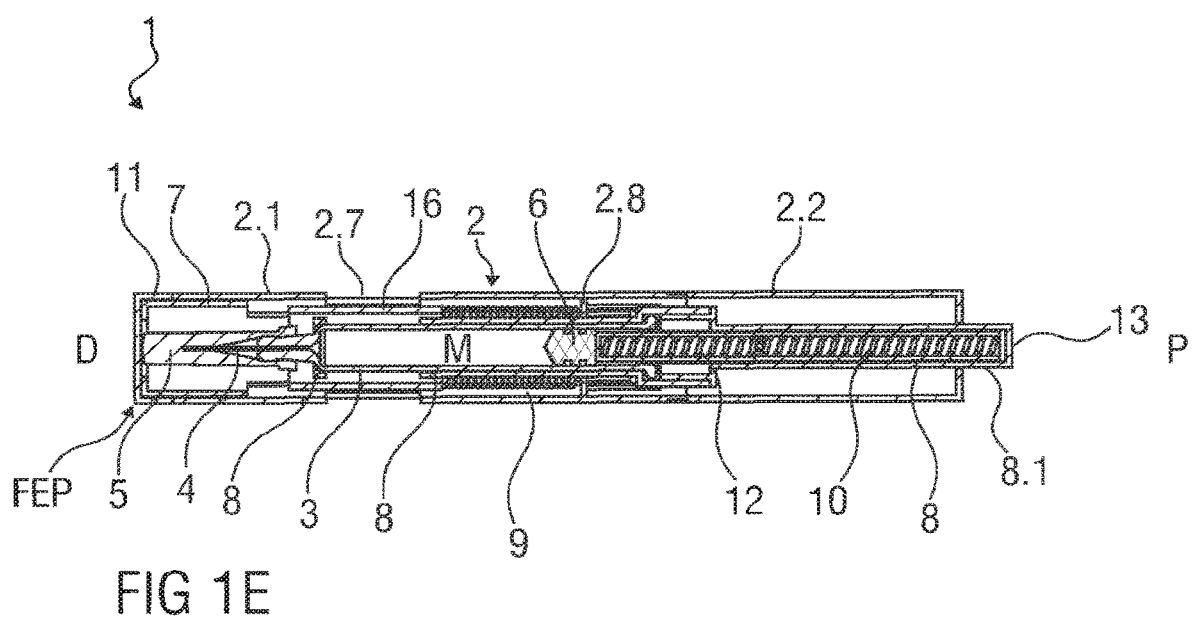
FIG. 1E is a longitudinal section of an exemplary embodiment of an autoinjector prior to use.
Figure 1F:
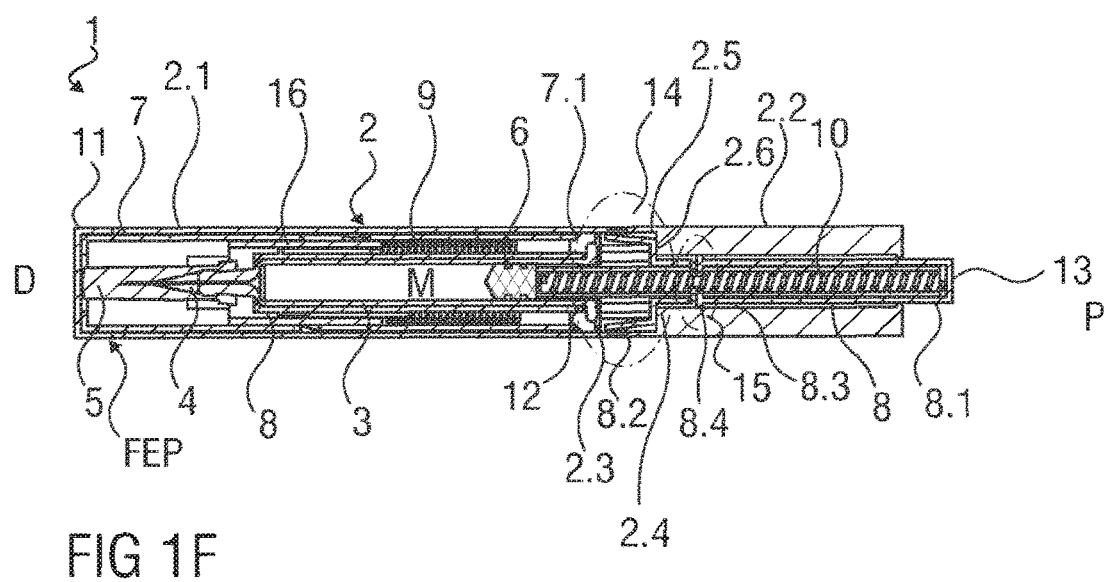
FIG. 1F is longitudinal section of an exemplary embodiment of an autoinjector prior to use.
Figure 2A:
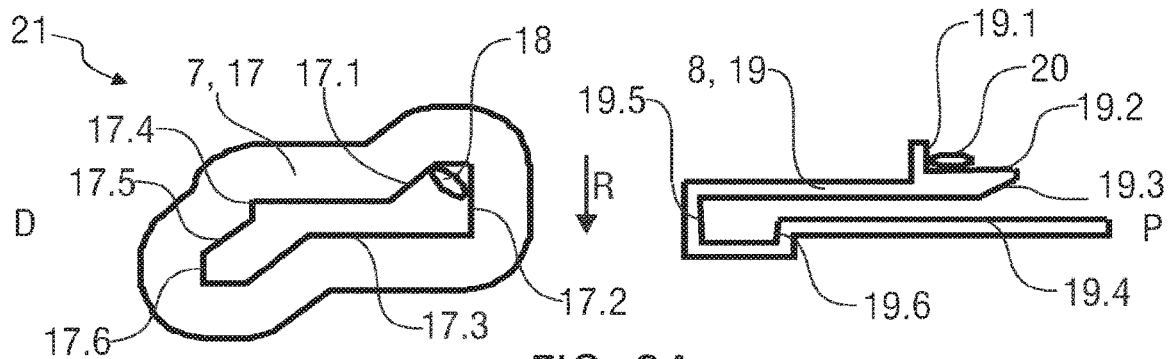
FIGS. 2A to 2H are schematic views of an exemplary embodiment of a control mechanism for an autoinjector in various states of operation of the autoinjector.
Figure 2B:
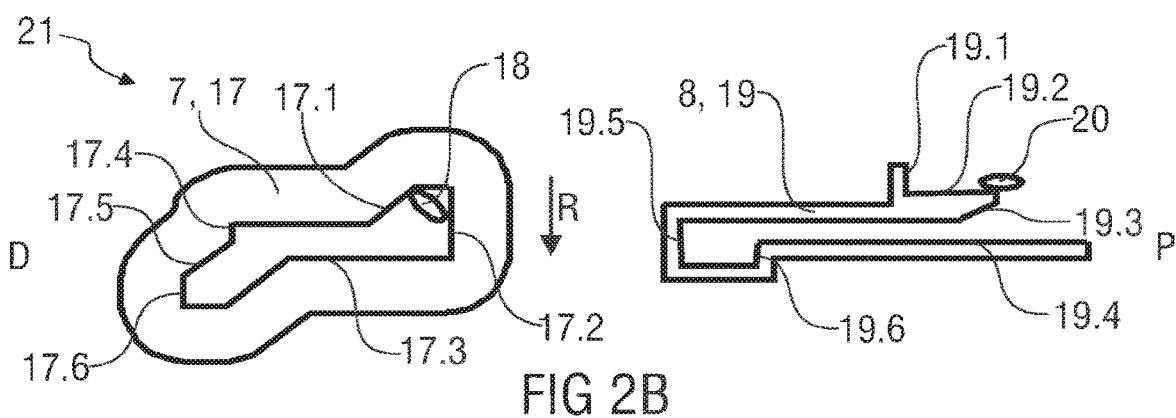
Figure 2C:
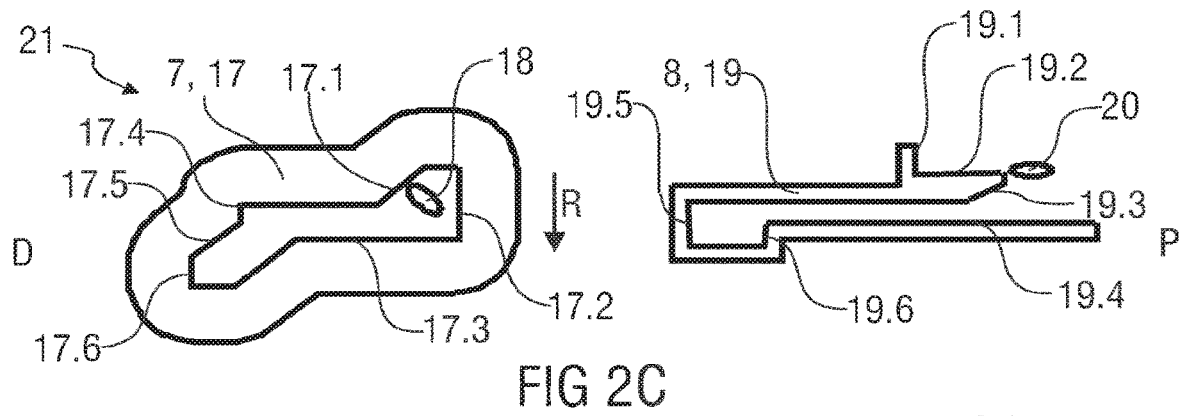
Figure 2D:
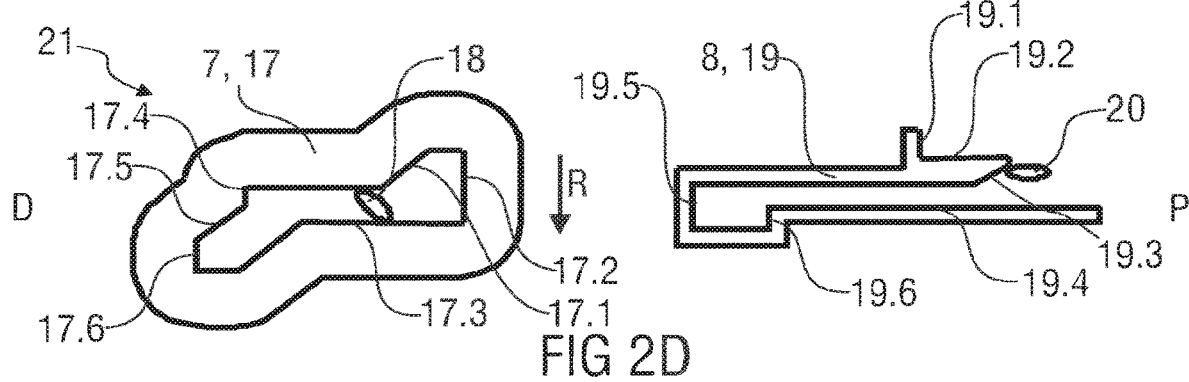
Figure 2E:
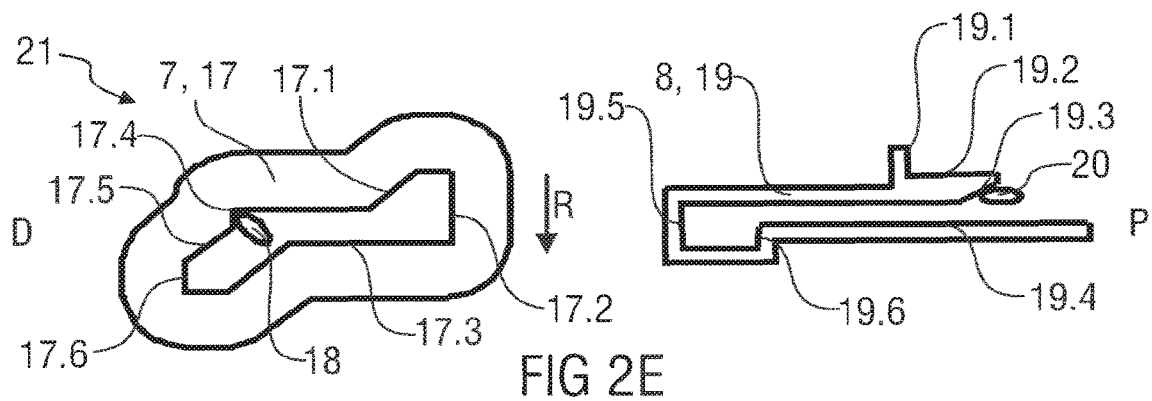
Figure 2F:
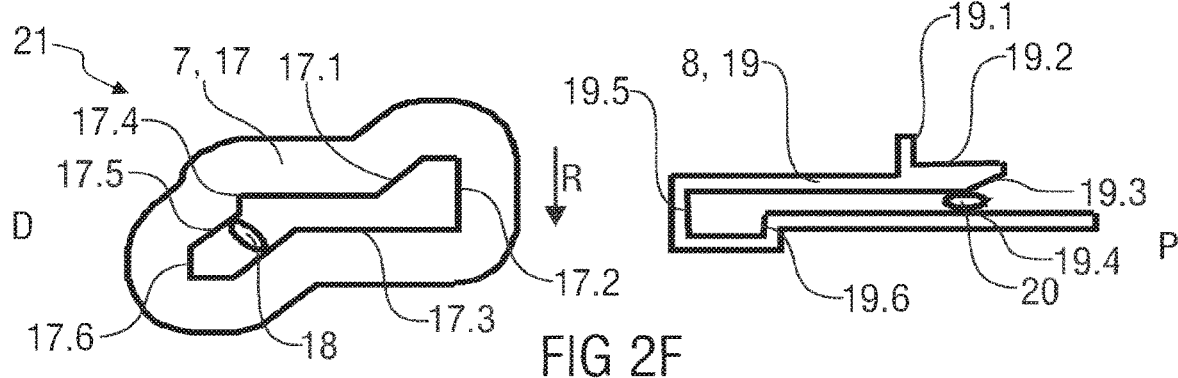
Figure 2G:
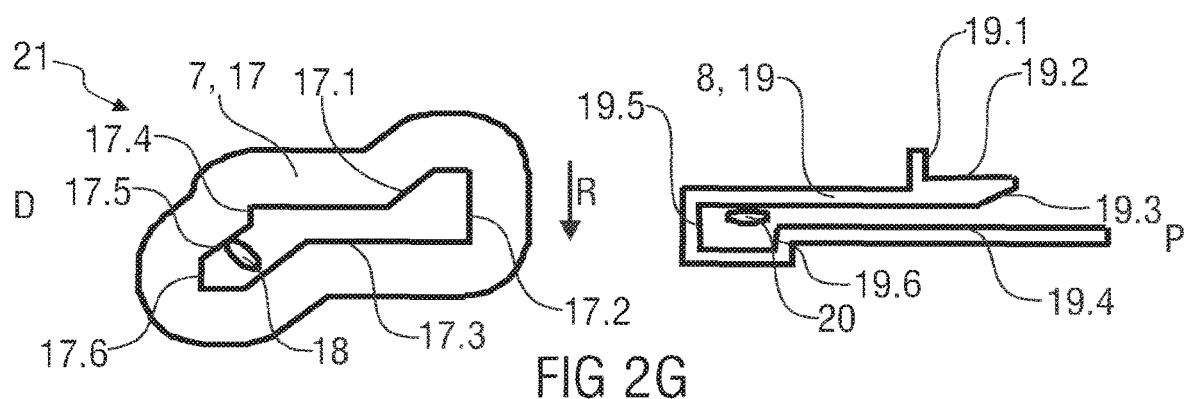
Figure 2H:
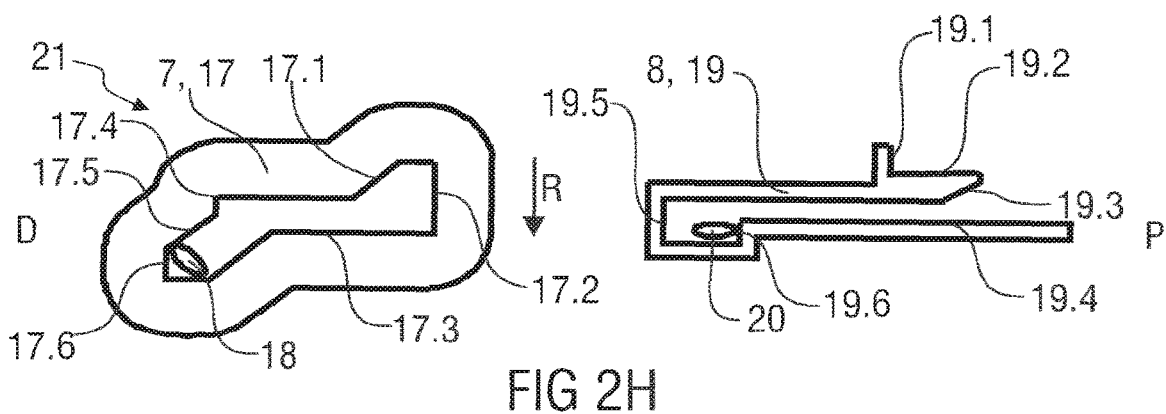

FIGS. 1A and 1B are different side views of an exemplary embodiment of an autoinjector 1 according to the present invention. The autoinjector 1 comprises a case 2 including a front case 2.1 and a rear case 2.2, and a needle shroud 7 telescoped within the case 2. A removable cap 11 is attached at a distal end of the case 2. The case 2 may comprise a viewing window 2.7, which may be a cut-out or transparent portion of the front case 2.1. FIG. 1C is a related longitudinal section of the autoinjector 1 with the case 2 and the needle shroud 7 removed for clarity. FIG. 1D is a related longitudinal section of the autoinjector 1 with the case 2 removed for clarity. FIG. 1E is a related longitudinal section of the autoinjector 1. FIG. 1F is another related longitudinal section of the autoinjector 1.

As shown in FIGS. 1E and 1F, the case 2 is adapted to slidably retain carrier which holds a medicament container, such as a syringe 3. The carrier, shown in a first axial position relative to the case 2, may include a syringe carrier (8) which is adapted to hold the syringe 3 (e.g., a pre-filled syringe having a needle 4 arranged at a distal end). When the autoinjector 1 and/or the syringe 3 are assembled, a protective needle sheath 5 may be removably coupled to the needle 4. The cap 11 may include an element (e.g., a barb, a hook, a narrowed section, etc.) arranged to engage the protective needle sheath 5 such that the protective needle sheath 5 is removed as the cap 11 is removed from the case 2. A stopper 6 is arranged for sealing the syringe 3 proximally and for displacing a medicament M contained in the syringe 3 through the needle 4. In other exemplary embodiments, the medicament container may be a cartridge which includes the medicament M and engages a removable needle.

In an exemplary embodiment, the needle shroud 7 is telescoped in the distal end of the case 2. A control spring 9 is arranged to bias the needle shroud 7 in a distal direction D relative to the case 2.

In an exemplary embodiment, a drive spring 10 (which may be a compression spring) is arranged within a proximal part 8.1 of the syringe carrier 8. A plunger 12 serves for forwarding a force of the drive spring 10 to the stopper 6. In an exemplary embodiment, the plunger 12 is hollow and telescoped within the proximal part 8.1 of the syringe carrier 8 wherein the drive spring 10 is arranged within the plunger 12 biasing the plunger 12 in the distal direction D relative to the syringe carrier 8. In an exemplary embodiment, the proximal part 8.1 of the syringe carrier 8 protrudes through an opening in a proximal end of the case 2 and serves as a trigger button 13. In other exemplary embodiments, a button overmold may be coupled to or integrally formed with the trigger button 13.

In an exemplary embodiment, a button lock mechanism 14 is arranged for locking the trigger button 13 such that it cannot be operated prior to depression of the needle shroud 7 and for unlocking the trigger button 13 on depression of the needle shroud 7 thus allowing operation of the trigger button 13. The button lock mechanism 14 comprises one or more compliant first beams 8.2 on the syringe carrier 8 adapted to abut ribs 2.3 within the case 2. This abutment prevents travel of the syringe carrier 8 in the distal direction D relative to the case 2. Furthermore, the button lock mechanism 14 comprises one or more ramp features 7.1 on a proximal end of the needle shroud 7 adapted to abut and radially inwardly deflect the compliant first beams 8.2 when the needle shroud 7 is depressed.

In an exemplary embodiment, a plunger release mechanism 15 is arranged for preventing release of the plunger 12 prior to the needle 4 reaching an insertion depth and for releasing the plunger 12 once the needle 4 reaches its insertion depth. The plunger release mechanism 15 comprises: one or more compliant second beams 8.3 with a respective first boss 8.4 arranged on the syringe carrier 8, a respective first opening 12.1 (best seen in FIG. 6F) radially arranged in the plunger 12 for engaging the first boss 8.4, a proximal narrow section 2.4 of the case 2 adapted to radially outwardly support the first boss 8.4 such that it cannot disengage the first opening 12.1 when the syringe carrier 8 is in a proximal position relative to the case 2, a wide section 2.5 distal of the narrow section 2.4 in the case 2 adapted to accommodate the first boss 8.4 upon radial outward deflection of the second beams 8.3 once the wide section 2.5 is axially aligned with the first boss 8.4 when the trigger button 13 has been pressed. At least one of the first boss 8.4 and the first opening 12.1 may be ramped to reduce the force necessary to deflect the second beam 8.3 under the load of the drive spring 10.

In an exemplary embodiment, a control mechanism 21 (illustratively shown in FIGS. 2A to 2H) is arranged for selectively applying the force of the control spring 9 to the syringe carrier 8 or to the needle shroud 7. The control mechanism 21 comprises a collar 16 having a shroud boss 18 adapted to engage a shroud slot 17 in the needle shroud 17 and a carrier boss 20 adapted to engage a carrier slot 19 in the syringe carrier 8. In an exemplary embodiment, the shroud boss 18 is disposed on an outer surface of the collar 16 and in a first plane angled with respect to a transverse axis of the collar 16, and the carrier boss 20 is disposed on an inner surface of the collar 16 in an axial plane, perpendicular to the transverse axis of the collar 16.

The control spring 9 is proximally grounded in the case 2 and distally bearing against the collar 16 which is movable axially and rotationally with respect to the case 2. In an exemplary embodiment, the collar 16 is arranged within the needle shroud 7 and over the syringe carrier 8. Prior to use, the control spring 9 may be compressed between the case 2 and the collar 16.

FIGS. 2A to 2H are schematic views of an exemplary embodiment of the control mechanism 21 different states corresponding to operation of the autoinjector 1. In an exemplary embodiment, the shroud slot 17 comprises an angled first surface 17.1, a transversal second surface 17.2, a longitudinal third surface 17.3, a transversal fourth surface 17.4, an angled fifth surface 17.5 and a transversal sixth surface 17.6. In an exemplary embodiment, the carrier slot 19 comprises a transversal first surface 19.1, a longitudinal second surface 19.2, an angled third surface 19.3, a longitudinal fourth surface 19.4, a transversal fifth surface 19.5 and a transversal sixth surface 19.6.

A sequence of operation of the autoinjector 1 is as follows:

Prior to use, the autoinjector 1 is in the state as illustrated in FIGS. 1A to 1F. If applicable, the autoinjector 1 may be removed from a packaging. The medicament M may be examined visually through the viewing window 2.7. The cap 11 can be removed by pulling it in the distal direction D away from the case 2 thereby also removing the protective needle sheath 5. The needle shroud 7 is in a first extended position FEP protruding distally beyond a distal end of the case 2.

Prior to use, the syringe carrier 8 is axially locked to the case 2, because the compliant first beams 8.2 on the syringe carrier 8 abut the ribs 2.3 within the case 2. The carrier boss 20 abuts the transversal first surface 19.1 of the carrier slot 19, preventing axial movement of the collar 16 in the distal direction D, and abuts the longitudinal second surface 19.2, preventing the collar 16 from rotating in a first rotational direction R relative to the case 2 (cf. FIG. 2A). The shroud boss 18 is located between the angled first surface 17.1 and the transversal second surface 17.2. The first extended position FEP is defined by the shroud boss 18 abutting the angled first surface 17.1 of the shroud slot 17.

Figure 3A:
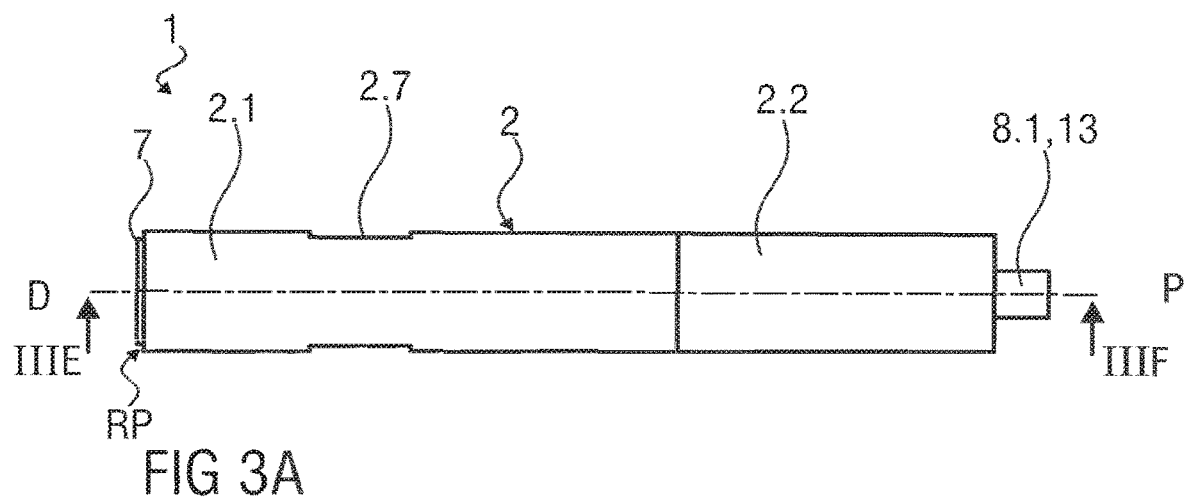
FIG. 3A is a side view of an exemplary embodiment of an autoinjector during use.
Figure 3B:
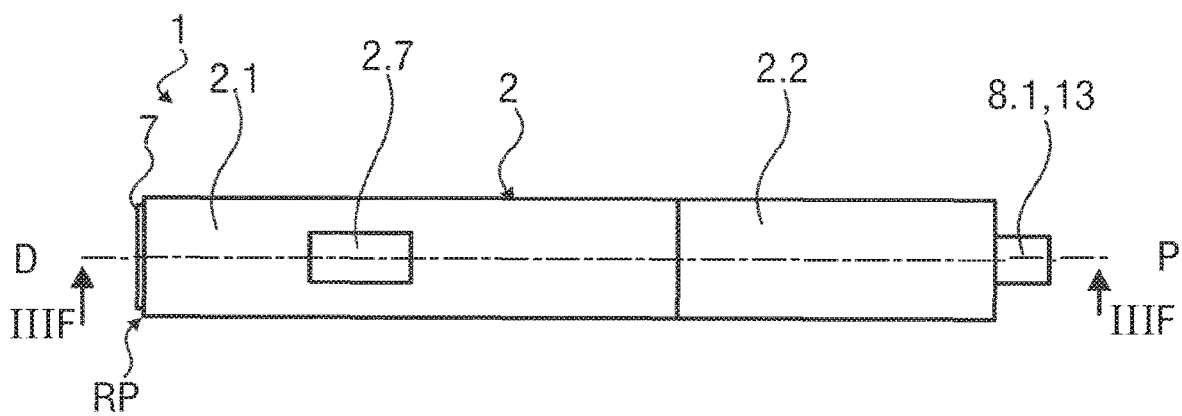
FIG. 3B is a side view of an exemplary embodiment of an autoinjector during use.
Figure 3C:
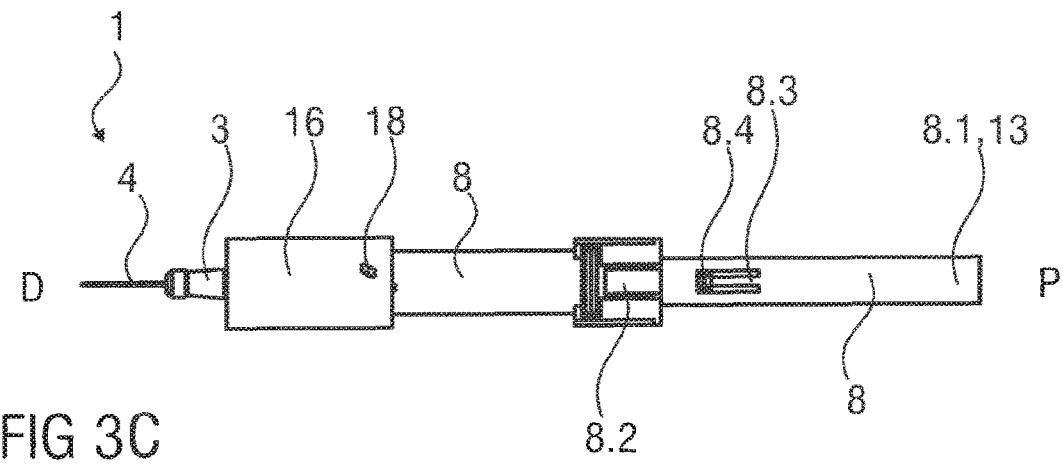
FIG. 3C is a longitudinal section of an exemplary embodiment of an autoinjector during use.
Figure 3D:
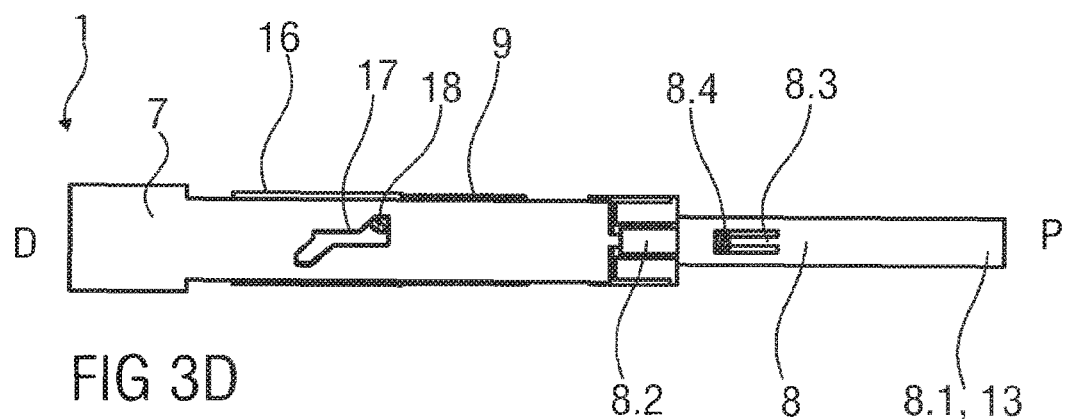
FIG. 3D is a longitudinal section of an exemplary embodiment of an autoinjector during use.
Figure 3E:
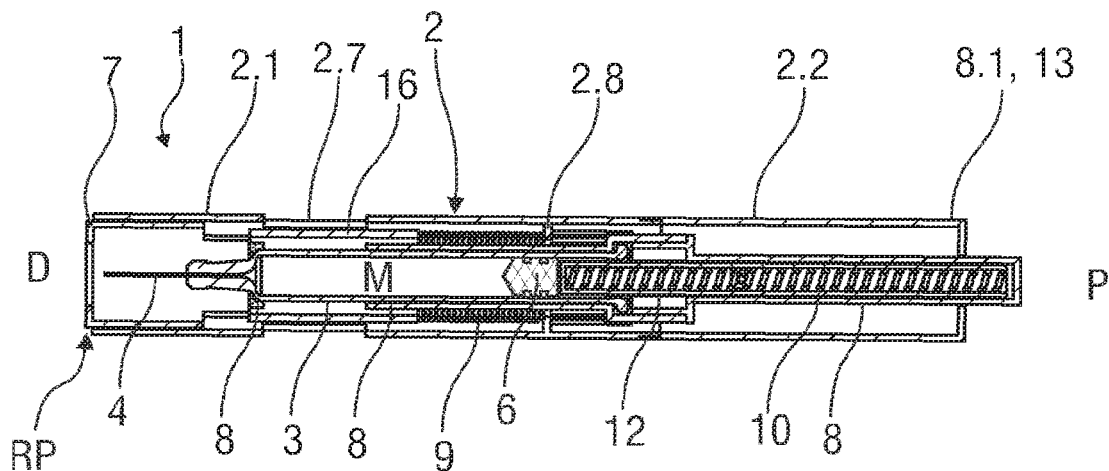
FIG. 3E is a longitudinal section of an exemplary embodiment of an autoinjector during use.
Figure 3F:
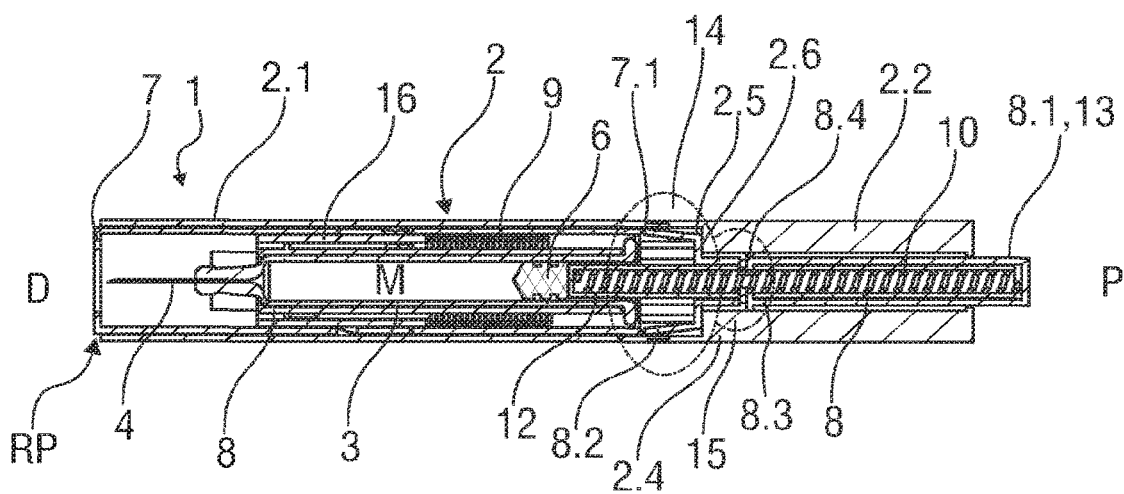
FIG. 3F is another longitudinal section of an exemplary embodiment of an autoinjector during use.

FIGS. 3A-F show an exemplary embodiment of the autoinjector 1 during use. FIGS. 3A and 3B are different side views of an exemplary embodiment of the autoinjector 1 after removal of the cap 11 and protective needle sheath 5, and after the needle shroud 7 has been moved into a retracted position RP relative to the case 2. FIG. 3C is a related longitudinal section of the autoinjector 1 with the case 2 and needle shroud 7 removed for clarity. FIG. 3D is a related longitudinal section of the autoinjector 1 with the case 2 removed for clarity. FIG. 3E is a related longitudinal section of the autoinjector 1. FIG. 3F is another related longitudinal section of the autoinjector 1.

When the autoinjector 1 is placed on and pressed against an injection site, the needle shroud 7 translates from the first extended position FEP to a retracted position RP relative to the case 2 against the biasing force of the control spring 9. As the needle shroud 7 translates from the first extended position FEP to the retracted position RP, the engagement of the shroud boss 18 and the angled first surface 17.1 pushes the collar 16 in the proximal direction P. As the first surface 17.1 is angled, a rotational force in the first rotational direction R is applied to the collar 16 as it translates in the proximal direction P, but the abutment of the carrier boss 20 on the longitudinal second surface 19.2 prevents the collar 16 from rotating relative to the case 2 (cf. FIG. 2B).

Also, as the needle shroud 7 translates from the first extended position FEP to the retracted position RP, the ramp features 7.1 of the needle shroud 7 engage the compliant first beams 8.2, causing them to deflect radially inward. When the needle shroud 7 is in the retracted position RP, the compliant first beams 8.2 are deflected radially due to the presence of the ramp features 7.1 on the needle shroud 7, but the compliant first beams 8.2 maintain engagement with the ribs 2.3. This prevents the syringe carrier 8 from translating relative to the case 2 until the trigger button 13 is pressed.

If the autoinjector 1 were removed from the injection site, the collar 16 and the needle shroud 7 would return to the positions shown in FIGS. 1A to 1F under the biasing force of the control spring 9.

Figure 4A:
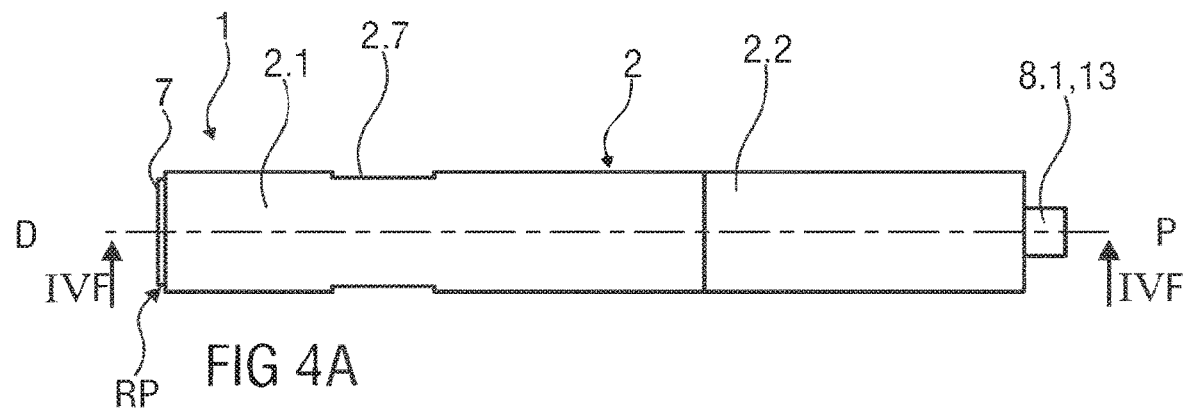
FIG. 4A is a side view of an exemplary embodiment of an autoinjector during use.
Figure 4B:
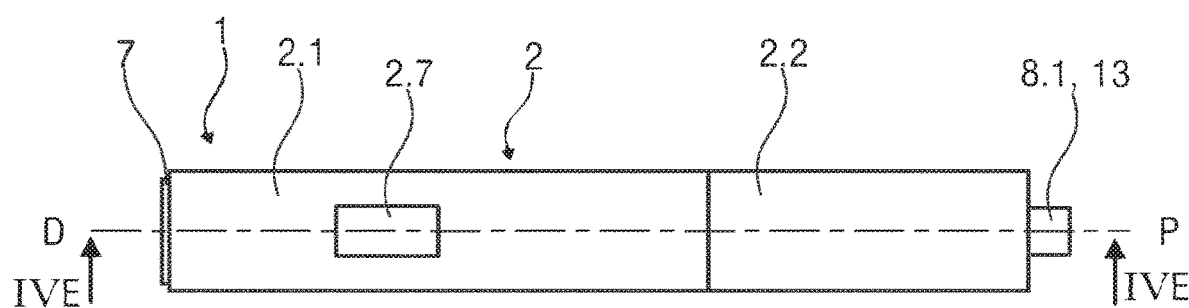
FIG. 4B is a side view of an exemplary embodiment of an autoinjector during use.
Figure 4C:
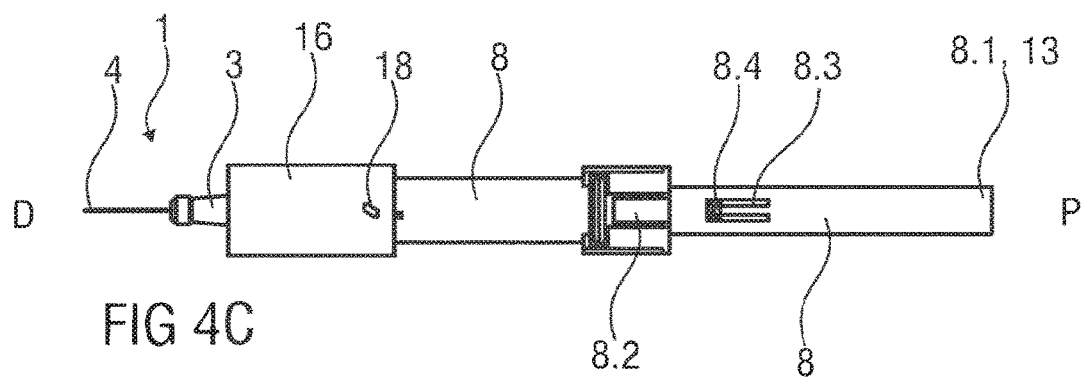
FIG. 4C is a longitudinal section of an exemplary embodiment of an autoinjector during use.
Figure 4D:
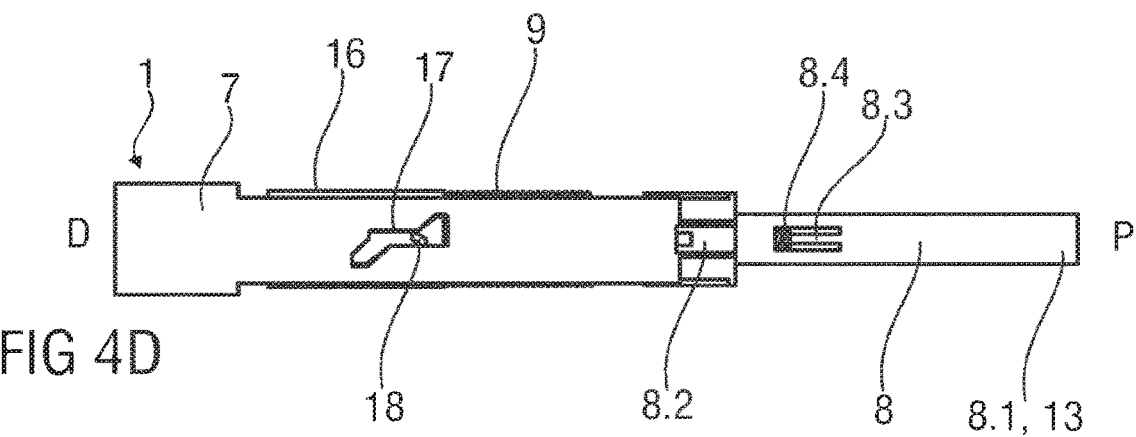
FIG. 4D is a longitudinal section of an exemplary embodiment of an autoinjector during use.
Figure 4E:
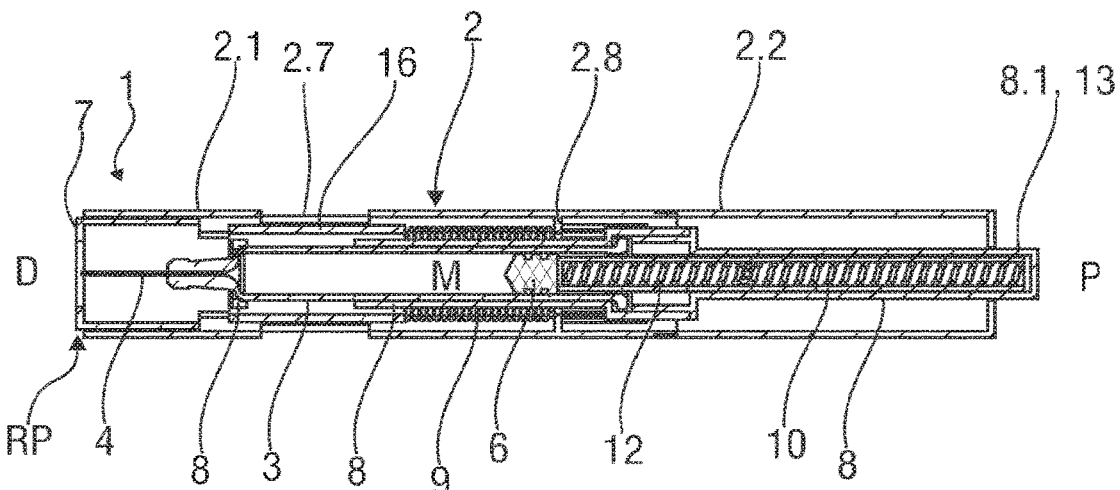
FIG. 4E is a longitudinal section of an exemplary embodiment of an autoinjector during use.
Figure 4F:
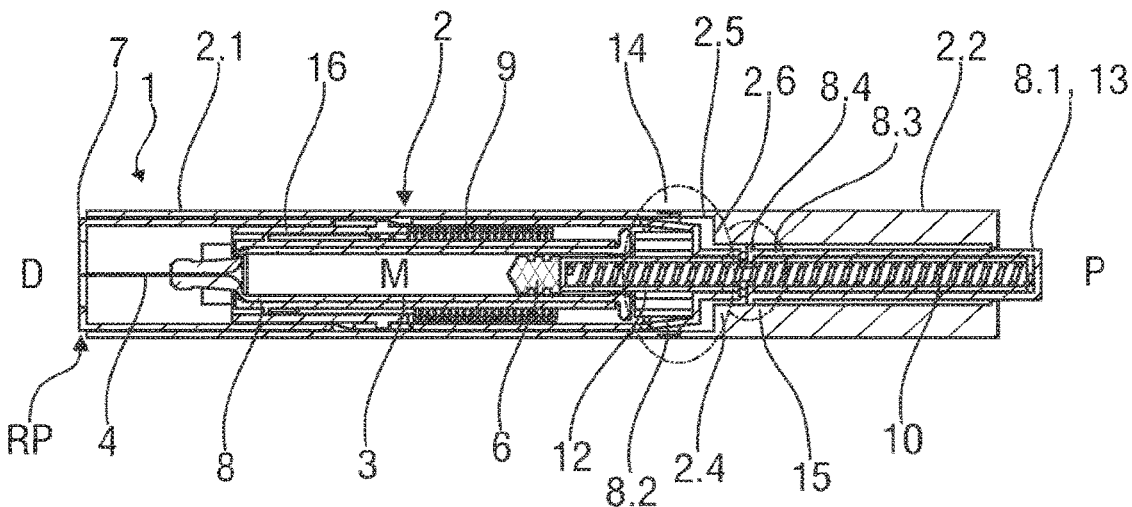
FIG. 4F is another longitudinal section of an exemplary embodiment of an autoinjector during use.

FIGS. 4A-F show an exemplary embodiment of the autoinjector 1 during use. FIGS. 4A and 4B are different side views of the autoinjector 1 after depression of the trigger button 13. FIG. 4C is a related longitudinal section of the autoinjector 1 with the case 2 and the needle shroud 7 removed for clarity. FIG. 4D is a related longitudinal section of the autoinjector 1 with the case 2 removed for clarity. FIG. 4E is a related longitudinal section of the autoinjector 1. FIG. 4F is another related longitudinal section of the autoinjector 1.

When the trigger button 13 is pressed, the compliant first beams 8.2 disengage the ribs 2.3, and the syringe carrier 8 moves in the distal direction D relative to the case 2. The carrier boss 20 disengages the longitudinal second surface 19.2 of the carrier slot 19 (cf. FIG. 2C) such that the rotational force on the shroud boss 18 by the angled first surface 17.1 causes the collar 16 to rotate in the first rotational direction R until it abuts the longitudinal third surface 17.3. When the shroud boss 18 abuts the longitudinal third surface 17.3, the carrier boss 20 has rotated into engagement with the angled third surface 19.3 of the carrier slot 19 (cf. FIG. 2D). The force of the control spring 9 is now applied to the syringe carrier 8.

Figure 5A:
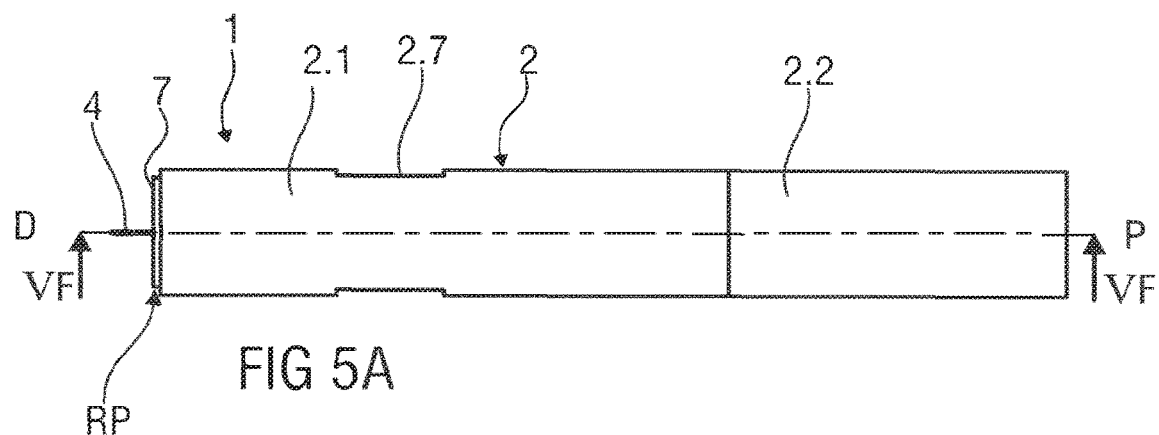
FIG. 5A is a side view of an exemplary embodiment of an autoinjector during use.
Figure 5B:
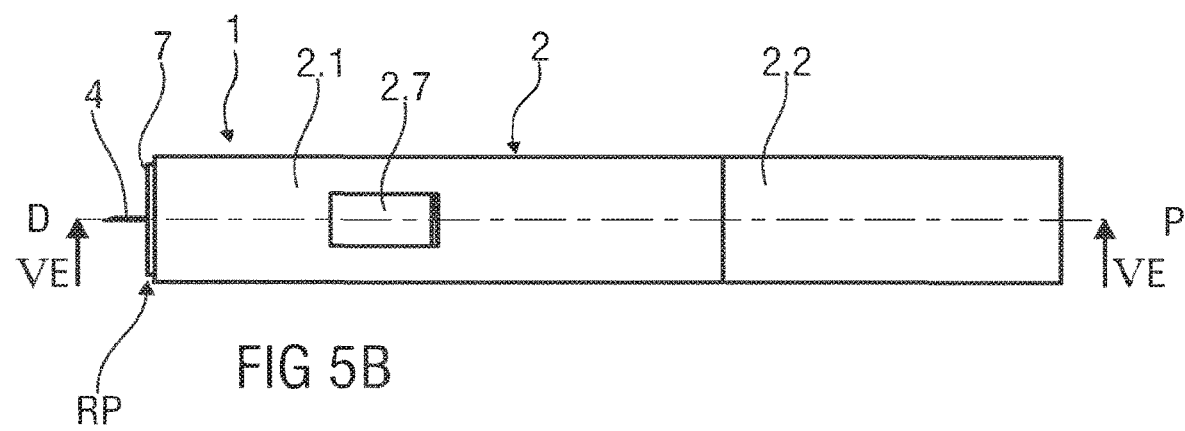
FIG. 5B is a side view of an exemplary embodiment of an autoinjector during use.
Figure 5C:
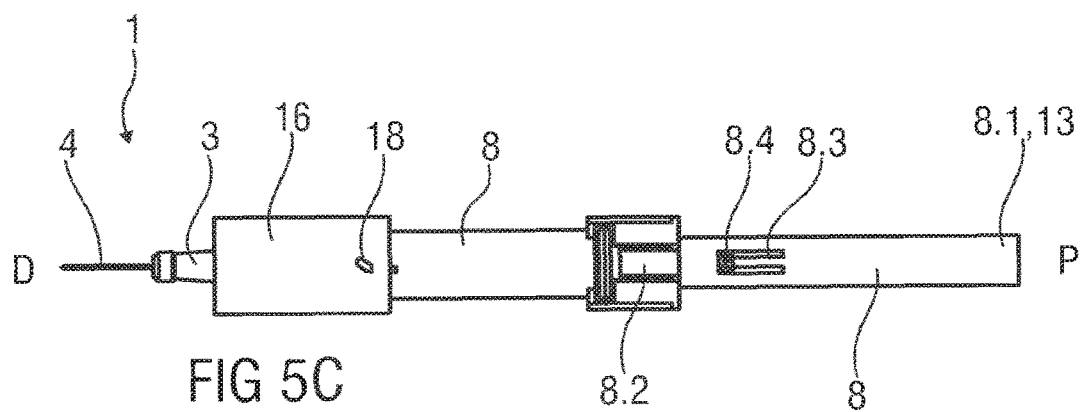
FIG. 5C is a longitudinal section of an exemplary embodiment of an autoinjector during use.
Figure 5D:
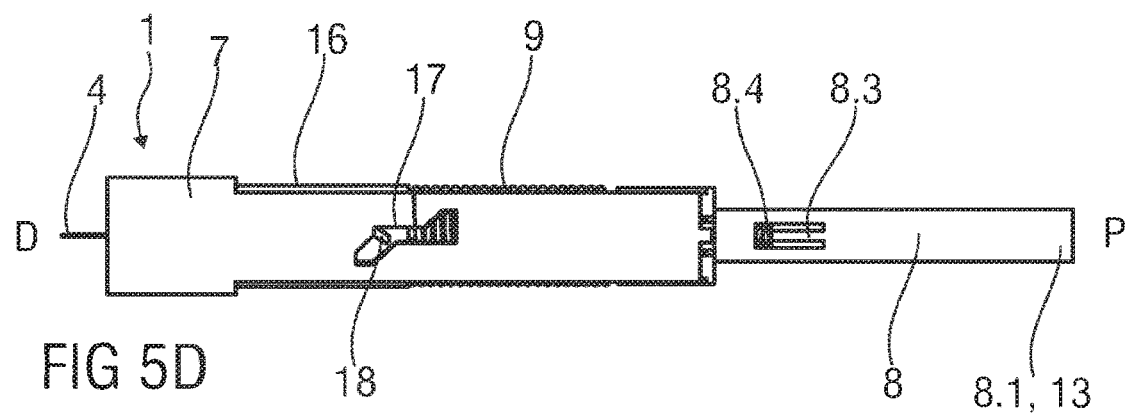
FIG. 5D is a longitudinal section of an exemplary embodiment of an autoinjector during use.
Figure 5E:
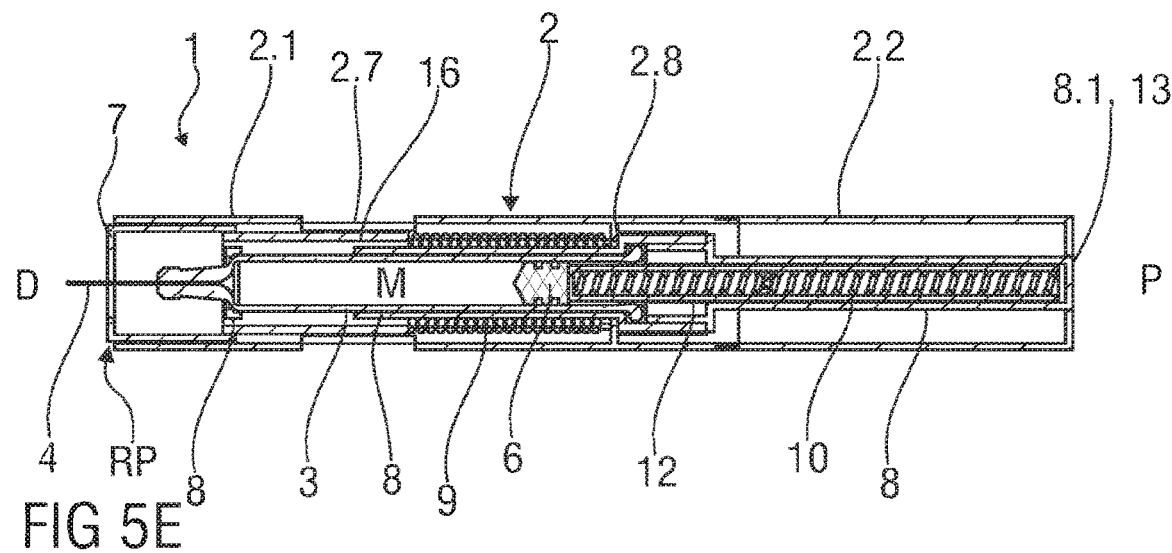
FIG. 5E is a longitudinal section of an exemplary embodiment of an autoinjector during use.
Figure 5F:
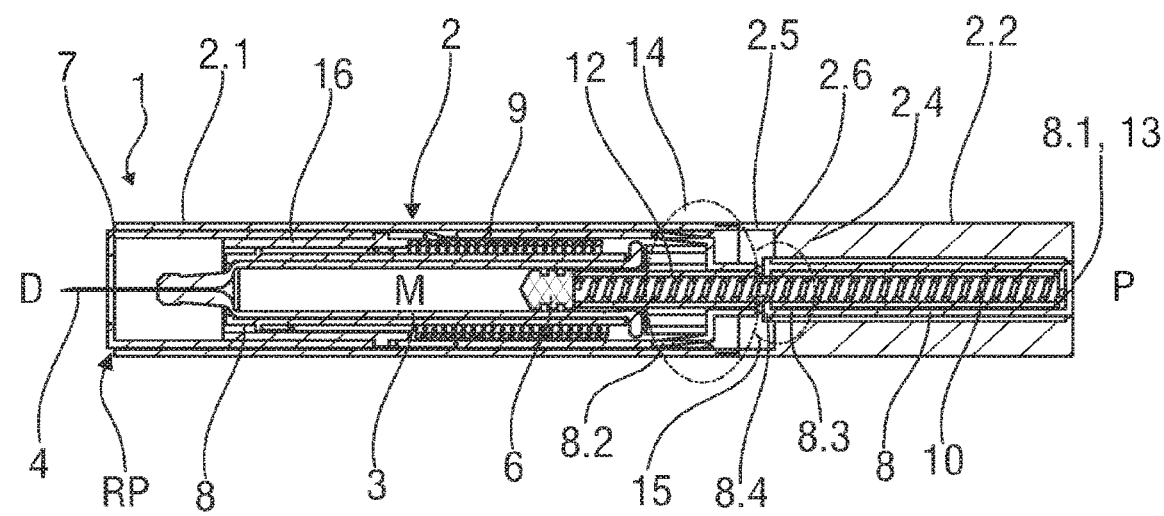
FIG. 5F is another longitudinal section of an exemplary embodiment of an autoinjector during use.

FIGS. 5A-F show an exemplary embodiment of the autoinjector 1 during use. FIGS. 5A and 5B are different side views of the autoinjector 1 with the needle 4 extending from the case 2. FIG. 5C is a related longitudinal section of the autoinjector 1 with the case 2 and needle shroud removed for clarity. FIG. 5D is a related longitudinal section of the autoinjector 1 with the case 2 removed for clarity. FIG. 5E is a related longitudinal section of the autoinjector 1. FIG. 5F is another related longitudinal section of the autoinjector 1.

When the shroud boss 18 abuts the longitudinal third surface 17.3 and the carrier boss 20 abuts the angled third surface 19.3, the force of the control spring 9 pushes the syringe carrier 8 in the distal direction D relative to the case 2 until the syringe carrier 8 abuts a front stop 2.8 on the case 2. The shroud boss 18 abuts transversal fourth surface 17.4 of the shroud slot 17 (cf. FIG. 2E). This axial translation of the syringe carrier 8 results in insertion of the needle 4 into the injection site.

As the syringe carrier 8 translates under the force of the control spring 9, the compliant second beams 8.3 reach the wide section 2.5 of the case 2, such that the plunger 12, under load from the drive spring 10, deflects the first boss 8.4 on the compliant beam 8.3 radially outwards. The first boss 8.4 disengages the first opening 12.1 in the plunger 12, and the plunger 12 is released from the syringe carrier 8, advancing the stopper 6 within the syringe 3 and ejecting the medicament M through the needle 4. In an exemplary embodiment, release of the plunger 12 from the syringe carrier 8 may provide an audible and/or tactile feedback to indicate that the injection has started. Progress of the medicament delivery can be observed through the viewing window 2.7 by examining movement of the plunger 12. Visibility of the plunger 12 in the viewing window 2.7 may also help differentiate between a used autoinjector and an unused autoinjector.

After the syringe carrier 8 has abutted the front stop 2.8 and ceased axial translation relative to the case 2, the force of the control spring 9 pushes the collar 16 in the distal direction D, and a rotational force is applied to the carrier boss 20 by the angled third surface 19.3 (cf. FIG. 2F) of the carrier slot 19. Because the shroud boss 18 abuts the transversal fourth surface 17.4, it is no longer rotationally supported by the longitudinal third surface 17.3, allowing the collar 16 to rotate in the first rotational direction R. The collar 16 rotates in the first rotational direction R until the carrier boss 20 abuts the longitudinal fourth surface 19.4, and the shroud boss 18 abuts the angled fifth surface 17.5. Because the autoinjector 1 is being held in place on the injection site, the collar 16 remains in the position shown in FIG. 2F.

Figure 6A:
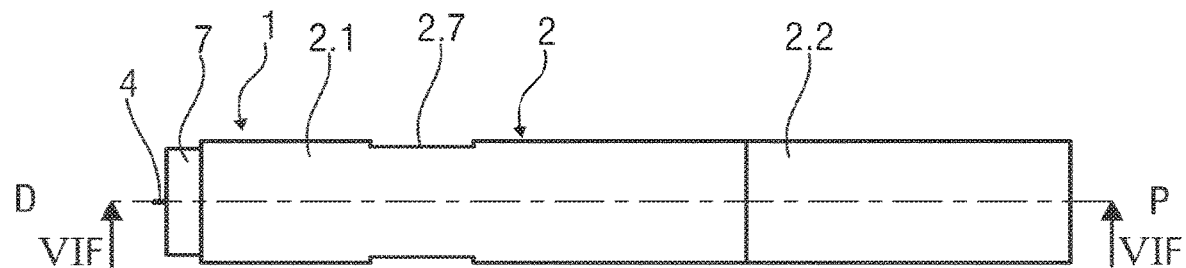
FIG. 6A is a side view of an exemplary embodiment of an autoinjector after use.
Figure 6B:
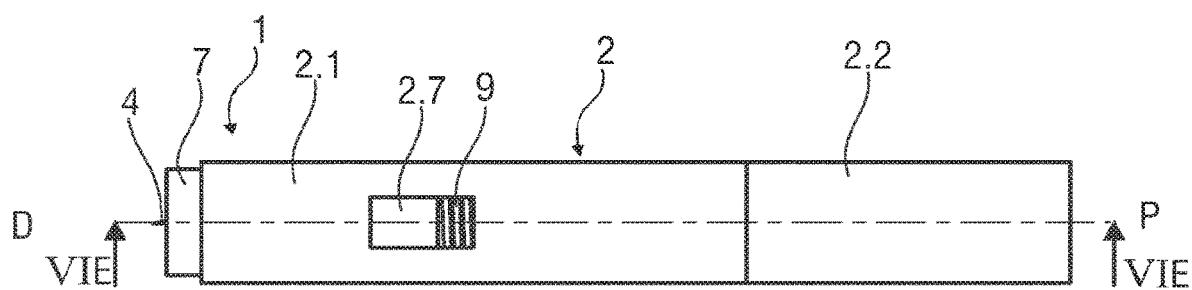
FIG. 6B is a side view of an exemplary embodiment of an autoinjector after use.
Figure 6C:
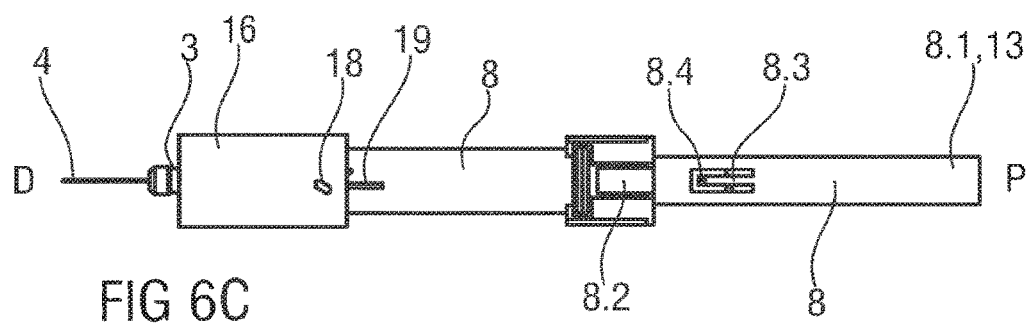
FIG. 6C is a longitudinal section of an exemplary embodiment of an autoinjector after use.
Figure 6D:
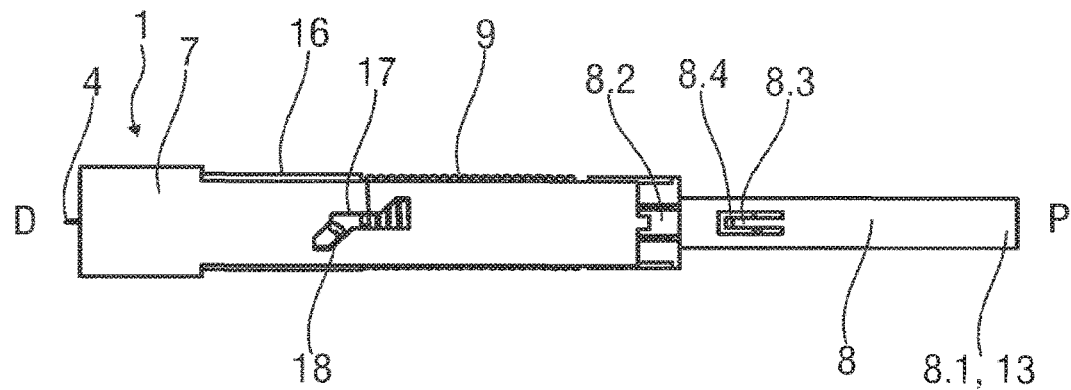
FIG. 6D is a longitudinal section of an exemplary embodiment of an autoinjector after use.
Figure 6E:
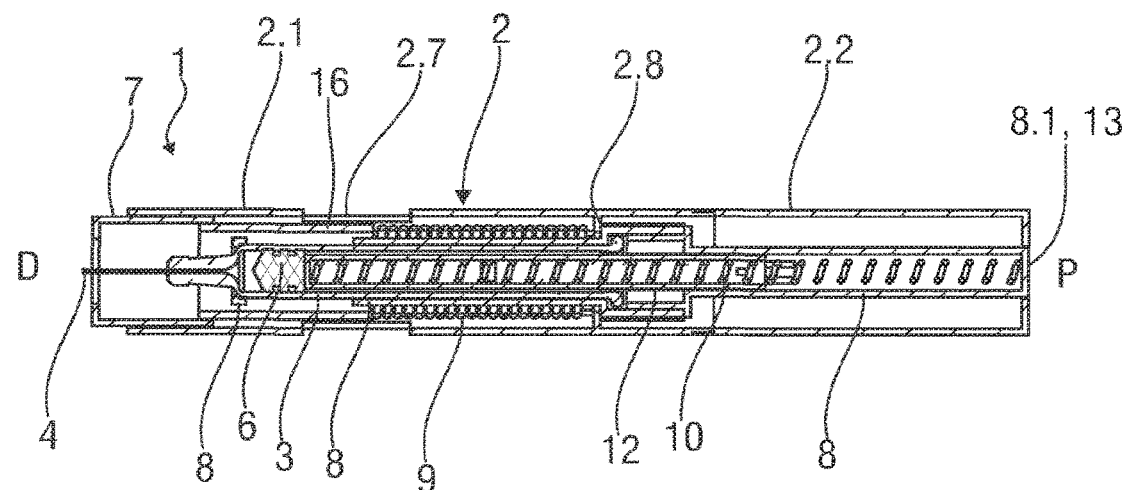
FIG. 6E is a longitudinal section of an exemplary embodiment of an autoinjector after use.
Figure 6F:
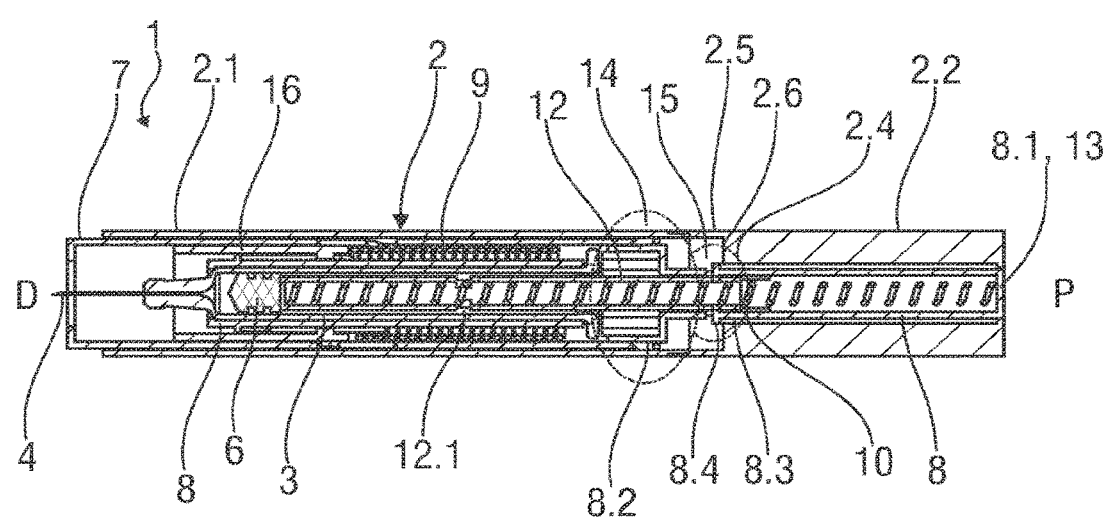
FIG. 6F is another longitudinal section of an exemplary embodiment of an autoinjector after use.

FIGS. 6A-F show an exemplary embodiment of the autoinjector 1 after use. FIGS. 6A and 6B are different side views of the autoinjector 1 with the syringe 3 emptied. FIG. 6C is a related longitudinal section of the autoinjector 1 with the case 2 and needle shroud removed for clarity. FIG. 6D is a related longitudinal section of the autoinjector 1 with the case 2 removed for clarity. FIG. 6E is a related longitudinal section of the autoinjector 1. FIG. 6F is another related longitudinal section of the autoinjector 1.

As shown in FIGS. 6A-F, when the autoinjector 1 is removed from the injection site, the needle shroud 7 translates relative to the case 2 from the retracted position RP toward a second extended position SEP.

Figure 7A:
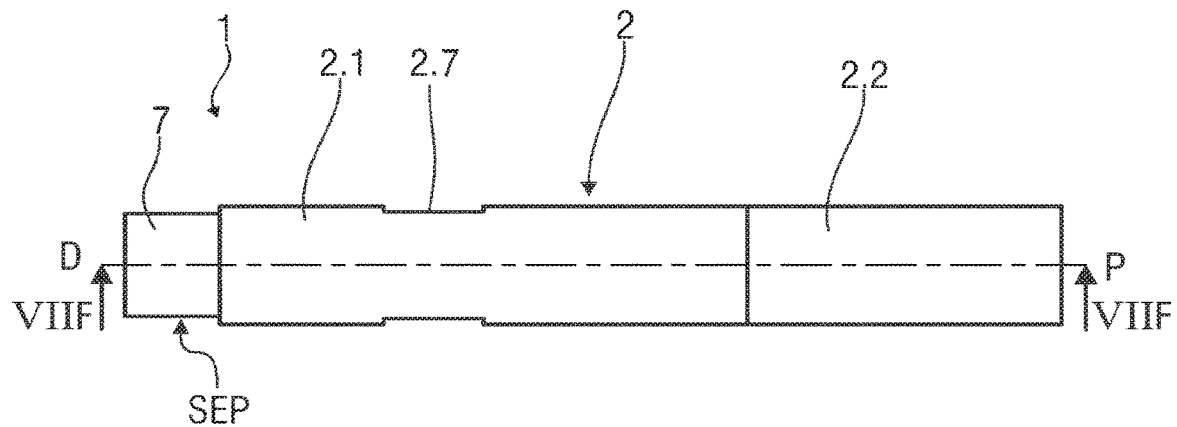
FIG. 7A is a side view of an exemplary embodiment of an autoinjector after use.
Figure 7B:
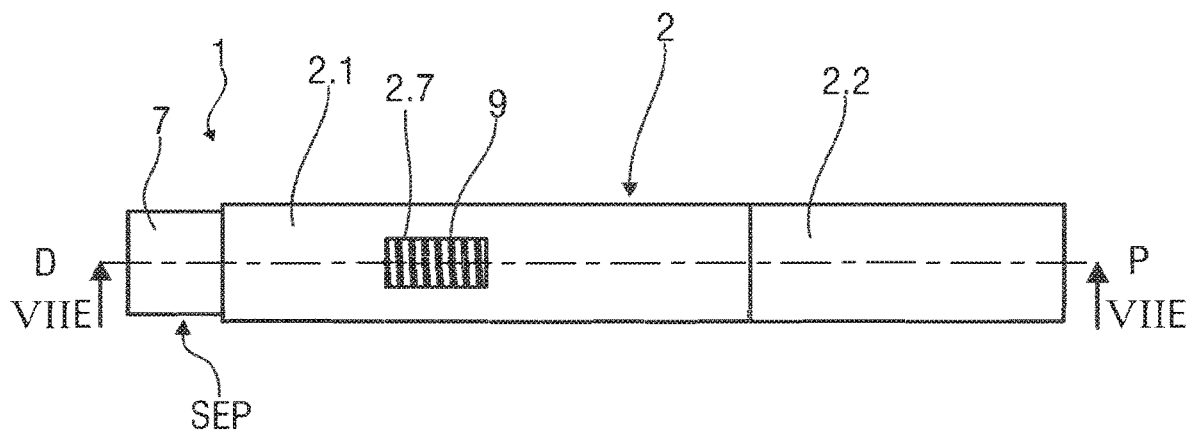
FIG. 7B is a side view of an exemplary embodiment of an autoinjector after use.
Figure 7C:
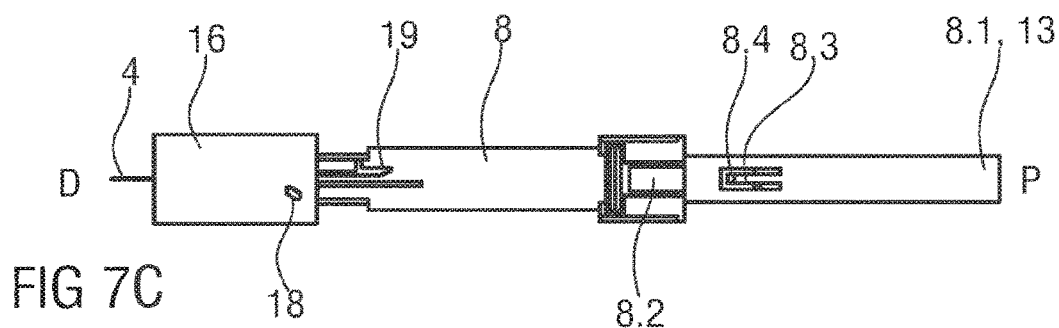
FIG. 7C is a longitudinal section of an exemplary embodiment of an autoinjector after use.

FIGS. 7A-F show an exemplary embodiment of the autoinjector after use. FIGS. 7A and 7B are different side views of the autoinjector 1 removed from the injection site with the needle shroud 7 in the second extended position. FIG. 7C is a related longitudinal section of the autoinjector 1 with the case 2 and needle shroud removed for clarity. FIG. 7D is a related longitudinal section of the autoinjector 1 with the case 2 removed for clarity. FIG. 7E is a related longitudinal section of the autoinjector 1. FIG. 7F is another related longitudinal section of the autoinjector 1.

When the autoinjector 1 is removed from the injection site, the force of the control spring 9 pushes the collar 16 in the distal direction D. Because the carrier boss 20 is abutting the longitudinal fourth surface 19.4 (and prevents the collar 16 from rotating), the force of the control spring 9 is applied by the shroud boss 18 on the angled fifth surface 17.5 to advance the needle shroud 7 in the distal direction D relative to the case 2 until the carrier boss 20 disengages the longitudinal fourth surface 19.4 (cf. FIG. 2G). A rotational force applied on the shroud boss 18 by the angled fifth surface 17.5 causes the collar 16 to rotate in the first rotational direction R, until the shroud boss 18 abuts the transversal sixth surface 17.6. The needle shroud 7 is now in a second extended position SEP (distal of the first extended position FEP) relative to the case 2. The needle shroud 7 is locked in the second extended position SEP, because if there is an attempt to move the needle shroud 7 proximally, the transversal sixth surface 17.6 will push the collar 16 in the proximal direction, but the carrier boss 20 will abut the transversal sixth surface 19.6 of the carrier slot 19 (cf. FIG. 2H). Because the syringe carrier 8 cannot move in the proximal direction P relative to the case 2 (because the first boss 8.4 abuts the narrow section 2.4 of the case 2), the collar 16 prevents the needle shroud 7 from retracting.

In another exemplary embodiment, the shroud boss 18 could be arranged on the needle shroud 7 and engaged in the shroud slot 17, which would be arranged in the collar 16. Likewise the carrier boss 20 could be arranged on the syringe carrier 8 and engaged in the carrier slot 19, which would be arranged in the collar 16.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(Ω-carboxyheptadecanoyl)-des(B30) human insulin and B29-N-(Ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39),
wherein the group -Lys6-NH2 may be bound to the C-terminus of the Exendin-4 derivative;

or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys) 6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4 (1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4 (1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp (O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2) 25, Asp28] Exendin-4(S1-39)-(Lys)6-NH2,
H-Asn-(Glu)5-des Pro36, Pro37, Pro38 [Met(O)14, Trp (O2)25, Asp28] Exendin-4(1-39)-(Lys)6-NH2,
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H-H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Those of skill in the art will understand that modifications (additions and/or removals) of various components of the apparatuses, methods and/or systems and embodiments described herein may be made without departing from the full scope and spirit of the present invention, which encompass such modifications and any and all equivalents thereof.

The invention claimed is:

1. An autoinjector comprising:
a case including a rib;
a needle shroud telescopically coupled to the case and movable between a first extended position, a retracted position and a locked second extended position;
a carrier arranged in the case and adapted to hold a medicament container;
a plunger slidably coupled to the carrier;
a drive spring arranged in the plunger, the drive spring biasing the plunger relative to the carrier, wherein the plunger is movable from a first axial position to a second axial position relative to the case; and
a collar slidably disposed in the case, the collar coupled to the needle shroud,
wherein the needle shroud is configured to move to the first extended position when the needle shroud is moved to the retracted position to advance the plunger to the second axial position,
wherein, in the second axial position, a portion of the plunger is arranged within the medicament container.

2. The autoinjector according to claim 1, wherein the carrier includes a compliant beam having a boss adapted to engage an opening in the plunger when the carrier is in a first axial position.

3. The autoinjector according to claim 2, wherein the boss is adapted to engage the case when the carrier is in a second axial position.

4. The autoinjector according to claim 1, wherein the collar includes a first boss adapted to engage a slot in the case and a second boss adapted to engage a plunger boss on the plunger.

5. The autoinjector according to claim 1, wherein the collar is in a first angular position relative to the case when the needle shroud is in the first extended position and the carrier is in a first axial position.

6. The autoinjector according to claim 5, wherein the collar is configured to rotate to a second angular position relative to the case when the needle shroud moves from the first extended position to the retracted position.

7. The autoinjector according to claim 1, wherein the collar is configured to translate proximally relative to the case when the needle shroud moves from the first extended position to the retracted position.

8. The autoinjector according to claim 7, wherein the collar is configured to translate distally relative to the case when the needle shroud is in the retracted position and the carrier moves from a first axial position to a second axial position.

9. The autoinjector according to claim 8, wherein the carrier includes a compliant beam having a boss adapted to engage an opening in the plunger when the carrier is in the first axial position, and wherein the boss is configured to disengage from the opening and abut the case when the carrier is in the second axial position.

10. The autoinjector according to claim 8, wherein the plunger is configured to translate axially relative to the carrier under a force of the drive spring advancing the plunger from the first axial position to the second axial position relative to the case.

11. The autoinjector according to claim 10, wherein the collar rotates to a third angular position relative to the case and translates with the needle shroud distally relative to the case when the carrier is moved to a third axial position.

12. The autoinjector according to claim 10, wherein the collar is configured to rotate to a fourth angular position relative to the case when the needle shroud is moved to the locked second extended position.

13. The autoinjector according to claim 12, wherein the collar includes a first boss adapted to engage a slot in the case and a second boss adapted to engage a plunger boss on the plunger, and wherein the first boss is adapted to abut a surface in a carrier slot of the carrier when the collar is in the fourth angular position and the needle shroud is in the locked second extended position.

14. The autoinjector according to claim 13, wherein engagement of the second boss and the plunger boss substantially fixes the collar in an axial position relative to the case.

15. The autoinjector according to claim 1, further comprising:
a control spring biasing the collar relative to the case.

16. The autoinjector according to claim 1, wherein the carrier includes a compliant beam adapted to engage the rib when the carrier is in first and second axial positions.

17. The autoinjector according to claim 16, wherein the needle shroud includes a ramp adapted to engage and deflect a plunger boss of the collar as the needle shroud translates from the first extended position to the retracted position.

18. A drive mechanism for a medicament delivery device, the drive mechanism comprising:
a needle shroud movable between a first extended position, a retracted position and a locked second extended position;
a plunger movable from a first axial position to a second axial position;
a drive spring arranged in the plunger, the drive spring configured to bias the plunger toward the second axial position; and
a collar coupled to the needle shroud,
wherein the needle shroud is configured to move to the first extended position when the needle shroud is moved to the retracted position to advance the plunger to the second axial position,
wherein, in the second axial position, a portion of the plunger is arranged within the medicament container.

19. The drive mechanism according to claim 18, further comprising a carrier adapted to hold a medicament container, wherein the plunger is slidably coupled to the carrier, and wherein the carrier includes a compliant beam having a boss adapted to engage an opening in the plunger when the carrier is in a first axial position.

20. An autoinjector comprising:
a case including a rib;
a needle shroud telescopically coupled to the case and movable between a first extended position, a retracted position and a locked second extended position;
a carrier arranged in the case and adapted to hold a medicament container;
a plunger slidably coupled to the carrier, wherein the plunger is arranged to abut a stopper within the medicament container;
a drive spring arranged in the plunger, the drive spring biasing the plunger relative to the carrier, wherein the plunger is movable from a first axial position to a second axial position relative to the case; and
a collar slidably disposed in the case, the collar coupled to the needle shroud,
wherein the needle shroud is configured to move to the first extended position when the needle shroud is moved to the retracted position to advance the plunger to the second axial position.

* * * * *

UNITED STATES PATENT AND TRADEMARK OFFICE
CERTIFICATE OF CORRECTION

PATENT NO. : 11,077,257 B2
APPLICATION NO. : 16/355691
DATED : August 3, 2021
INVENTOR(S) : Thomas Kemp Page 1 of 1

It is certified that error appears in the above-identified patent and that said Letters Patent is hereby corrected as shown below:

In the Claims

In Column 14, Line 23, Claim 18, delete "the" and insert -- a --

In Column 14, Line 25, Claim 19, delete "a medicament" and insert -- the medicament --

Signed and Sealed this
Twenty-fourth Day of January, 2023

Katherine Kelly Vidal
*Director of the United States Patent and Trademark Office*